US012770731B2

(12) United States Patent
Singh et al.

(10) Patent No.: US 12,770,731 B2
(45) Date of Patent: Oct. 20, 2026

(54) DISAGGREGATED LOW-FIELD MAGNETIC RESONANCE IMAGING WITH SECURE METASURFACES-ENHANCED PRIVATE WIRELESS NETWORK

(71) Applicant: Dell Products L.P., Round Rock, TX (US)

(72) Inventors: Tejinder Singh, Manotick (CA); Navjot Kaur Khaira, Manotick (CA); Raja Neogi, Portland, OR (US)

(73) Assignee: DELL PRODUCTS L.P., Round Rock, TX (US)

( * ) Notice: Subject to any disclaimer, the term of this patent is extended or adjusted under 35 U.S.C. 154(b) by 305 days.

(21) Appl. No.: 18/656,388

(22) Filed: May 6, 2024

(65) Prior Publication Data

US 2025/0342940 A1 Nov. 6, 2025

(51) Int. Cl.

| | |
|---|---|
| ***G16H 30/40*** | (2018.01) |
| ***G06T 3/4053*** | (2024.01) |
| ***G06V 20/70*** | (2022.01) |

(52) U.S. Cl.

CPC ........... *G16H 30/40* (2018.01); *G06T 3/4053* (2013.01); *G06V 20/70* (2022.01)

(58) Field of Classification Search

CPC ...... G16H 30/40; G16H 30/20; G06T 3/4053; G06V 20/70; G06V 2201/03

See application file for complete search history.

(56) References Cited

U.S. PATENT DOCUMENTS

| | | | | |
|---|---|---|---|---|
| 10,607,331 B1 * | 3/2020 | Tandia | ................. | G06V 40/172 |
| 2002/0038226 A1 * | 3/2002 | Tyus | ...................... | G16H 30/20<br>705/2 |

(Continued)

FOREIGN PATENT DOCUMENTS

| | | | | |
|---|---|---|---|---|
| CA | 3085441 A1 * | 7/2019 | ............... | G06T 7/11 |
| CN | 111798377 A * | 10/2020 | ............ | G06N 3/045 |

(Continued)

OTHER PUBLICATIONS

Güven, Sara Altun, and Muhammed Fatih Talu. "Brain MRI high resolution image creation and segmentation with the new GAN method." Biomedical Signal Processing and Control 80 (2023): 104246. (Year: 2023).*

(Continued)

*Primary Examiner* — Carol W Chan

(74) *Attorney, Agent, or Firm* — Amin, Turocy & Watson, LLP

(57) ABSTRACT

The technology described herein is directed towards using a trained artificial intelligence (AI) model to generate high-resolution images from lower resolution magnetic resonance imaging (MRI) images captured by a lower magnetic field strength MRI device. For security and privacy, a reconfigurable intelligent surface can be used in the signal path to the trained model to thwart potential eavesdroppers. Also described is a trained AI annotator model that produces annotation data for annotating a generated high-resolution image. Local training using a cycle generative adversarial network, and based in part on federated learning, provides a highly-accurate low-resolution-to-high-resolution image generator model, while a conditional generative adversarial network provides a highly-accurate annotator model. A medical expert can thus analyze the highly-accurately generated high-resolution images with the benefit of annotation data to highlight any defects detected by the annotator model.

20 Claims, 14 Drawing Sheets

(56) References Cited

U.S. PATENT DOCUMENTS

| | | | | |
|---|---|---|---|---|
| 2003/0140141 | A1* | 7/2003 | Mullen | G06F 11/2294 709/225 |
| 2004/0190795 | A1* | 9/2004 | Funahashi | H04L 63/0428 358/1.15 |
| 2019/0244399 | A1* | 8/2019 | Li | G01R 33/5608 |
| 2019/0304092 | A1* | 10/2019 | Akselrod-Ballin | G16H 30/40 |
| 2020/0034948 | A1* | 1/2020 | Park | G06T 5/70 |
| 2020/0202502 | A1* | 6/2020 | Tsymbalenko | G06T 5/60 |
| 2022/0004838 | A1* | 1/2022 | DiDonato | G06N 3/02 |
| 2022/0262471 | A1* | 8/2022 | Nakamura | G06F 40/169 |
| 2022/0351347 | A1* | 11/2022 | Yang | G06N 3/096 |

FOREIGN PATENT DOCUMENTS

| | | | | |
|---|---|---|---|---|
| CN | 114445273 | A * | 5/2022 | G06N 3/045 |
| CN | 117316424 | A * | 12/2023 | G01R 33/48 |
| EP | 4306983 | A1 * | 1/2024 | G01R 33/5608 |
| KR | 102628166 | B1 * | 1/2024 | G16H 30/40 |
| WO | WO-2022239897 | A1 * | 11/2022 | G06T 3/4053 |

OTHER PUBLICATIONS

Wu, Kun, et al. "Image synthesis in contrast MRI based on super resolution reconstruction with multi-refinement cycle-consistent generative adversarial networks." Journal of Intelligent Manufacturing 31, No. 5 (2020): 1215-1228. (Year: 2020).*

Chun, Jaehee, et al. "MRI super-resolution reconstruction for MRI-guided adaptive radiotherapy using cascaded deep learning: In the presence of limited training data and unknown translation model." Medical physics 46, No. 9 (2019): 4148-4164. (Year: 2019).*

Bulat, Adrian, Jing Yang, and Georgios Tzimiropoulos. "To learn image super-resolution, use a gan to learn how to do image degradation first." In Proceedings of the European conference on computer vision (ECCV), pp. 185-200. 2018. (Year: 2018).*

Translated version of CN 117316424 (Year: 2023).*

* cited by examiner

DISAGGREGATED LOW-FIELD MAGNETIC RESONANCE IMAGING WITH SECURE METASURFACES-ENHANCED PRIVATE WIRELESS NETWORK

BACKGROUND

Magnetic resonance imaging (MRI) machines are non-intrusive devices that provide three-dimensional views of a medical patient's internal structures. Typical machines output a magnetic field strength of about 1.5 to 3.0 Teslas (T), although stronger machines are becoming more commonplace. Such MRI machines with a room-scale footprint cost on the order of five million dollars each, and a given hospital may need several of them depending on the hospital's size.

MRI scans are associated with patient information, and thus need to be kept private. As such, when sending the private MRI data from the scanner (source endpoint) to an authorized receiving entity, consideration needs to be given to sending the MRI data over a secure communications link.

BRIEF DESCRIPTION OF THE DRAWINGS

The technology described herein is illustrated by way of example and not limited in the accompanying figures in which like reference numerals indicate similar elements and in which.

DETAILED DESCRIPTION

Figure 1:
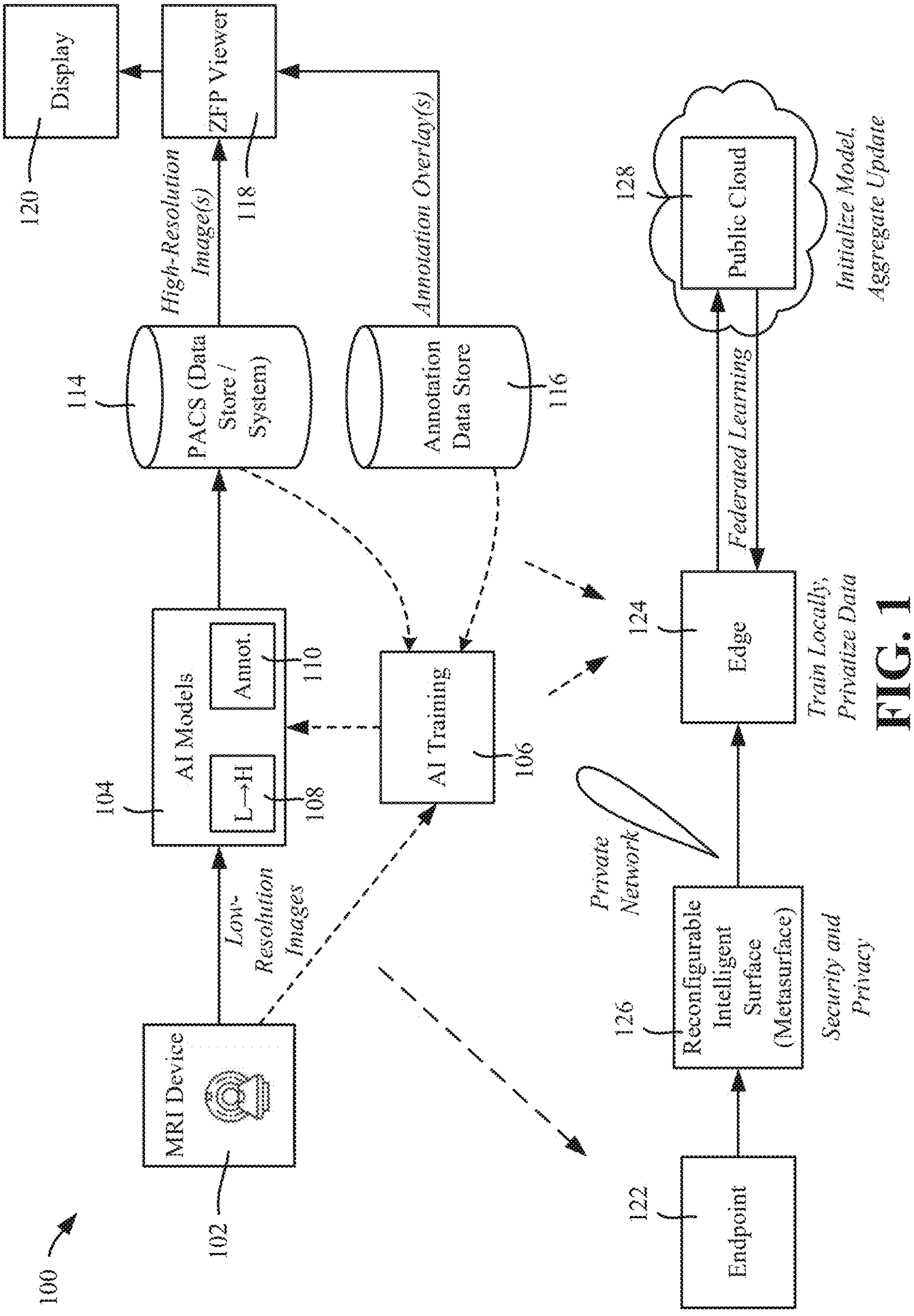
FIG. 1 is a representation of an example environment including a system in which a low magnetic field strength (e.g., portable) magnetic resonance imaging (MRI) device captures low-resolution images, which are securely transmitted to an edge cloud location for conversion by a trained model to high-resolution images, in accordance with various example embodiments and implementations of the subject disclosure.

The technology described herein is generally directed towards a modular (e.g., portable, approximately 0.5 tesla (T)) magnetic resonance imaging (MRI) device, and using its captured images to generate high-resolution images that are suitable for viewing and analyzing by medical professionals. In general, such a portable, lower magnetic field strength MRI device can be designed to cost approximately ten times less than a room-sized (>1.5T) MRI device, however the lower magnetic field strength produces lower quality (lower resolution images). As a result, portable MRIs are not used in sensitive medical procedures, as radiologists need sharper images to correctly interpret defects.

Described herein is predicting higher-resolution images from low-resolution image capture, with significantly high enough image quality/resolution to accurately view (and annotate) medical defects. Trained generative models that learn from actual images perform the upscaling of the resolution; in one implementation, a cycle generative adversarial network model is used to train the artificial intelligence/machine learning (AI/ML) low-resolution-to-high-resolution generator. Further, another trained model, with training data (including high-resolution images) specific to a medical procedure, performs automatic annotation for high-resolution images associated with that specific medical procedure, (e.g., analysis/diagnosis of a knee problem). Training of the models can be local, e.g., at an edge cloud location, and can be combined with federated learning from other models, which facilitates model initialization, aggregation and updating from the public cloud in a hybrid cloud solution for low-cost portable MRI devices.

Because capture and storage of MRI image data is private and by law needs to be carefully protected, one implementation described herein disaggregates the transmitting of patient data from the source (endpoint). To this end, private networking using a metasurface that retransmits received data signals from the source endpoint is used to provide security and privacy features through hardware-level encryption, which is highly valuable for securely transmitting patient data. For example, each image can be retransmitted as a hardware-encrypted image in a private 5G network, such that a received encrypted instance of the image can be hardware decrypted and used for subsequent analysis and diagnosis. Further, patient identification data associated with an MRI image can be disaggregated from the MRI image to provide anonymous training data.

It should be understood that any of the examples and/or descriptions herein are non-limiting. Thus, any of the embodiments, example embodiments, concepts, structures, functionalities or examples described herein are non-limiting, and the technology may be used in various ways that provide benefits and advantages in communications and computing in general.

Reference throughout this specification to "one embodiment," "an embodiment," "one implementation," "an implementation," etc. means that a particular feature, structure, characteristic and/or attribute described in connection with the embodiment/implementation can be included in at least one embodiment/implementation. Thus, the appearances of such a phrase "in one embodiment," "in an implementation," etc. in various places throughout this specification are not necessarily all referring to the same embodiment/implementation. Furthermore, the particular features, structures, characteristics and/or attributes may be combined in any suitable manner in one or more embodiments/implementations. Repetitive description of like elements employed in respective embodiments may be omitted for sake of brevity.

The detailed description is merely illustrative and is not intended to limit embodiments and/or application or uses of embodiments. Furthermore, there is no intention to be bound by any expressed or implied information presented in the preceding sections, or in the Detailed Description section. Further, it is to be understood that the present disclosure will be described in terms of a given illustrative architecture; however, other architectures, structures, materials and process features, and steps can be varied within the scope of the present disclosure.

It also should be noted that terms used herein, such as "optimize," "optimization," "optimal," "optimally" and the like only represent objectives to move towards a more optimal state, rather than necessarily obtaining ideal results. For example, "optimal" placement of a subnet means selecting a more optimal subnet over another option, rather than necessarily achieving an optimal result. Similarly, "maximize" means moving towards a maximal state (e.g., up to some processing capacity limit), not necessarily achieving such a state, and so on.

It will also be understood that when an element such as a layer, region or substrate is referred to as being "on" or "over" "atop" "above" "beneath" "below" and so forth with respect to another element, it can be directly on the other element or intervening elements can also be present. In contrast, only if and when an element is referred to as being "directly on" or "directly over" another element, are there no intervening element(s) present. Note that orientation is generally relative; e.g., "on" or "over" can be flipped, and if so, can be considered unchanged, even if technically appearing to be under or below/beneath when represented in a flipped orientation. It will also be understood that when an element is referred to as being "connected" or "coupled" to another element, it can be directly connected or coupled to the other element or intervening elements can be present. In contrast, only if and when an element is referred to as being "directly connected" or "directly coupled" to another element, are there no intervening element(s) present.

The following detailed description is merely illustrative and is not intended to limit embodiments and/or application or uses of embodiments. Furthermore, there is no intention to be bound by any expressed or implied information presented in the preceding sections, or in the Detailed Description section.

One or more example embodiments are now described with reference to the drawings, in which example components, graphs and/or operations are shown, and in which like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details, and that the subject disclosure may be embodied in many different forms and should not be construed as limited to the examples set forth herein.

FIG. 1 is a conceptual depiction of an example system 100 including a lower magnetic field strength (e.g., portable) MRI device 102 that communicates that captures low-resolution images for communication to receiving entities, including to AI models 104 (trained models) and to (an edge local AI training subsystem/training units) 106. The AI models 104 include a low-resolution image-to-high-resolution image (L→H) conversion AI model 108 as described herein, which generates the (synthetic) high-resolution images for analysis, e.g., as super-resolution images. Further, once a high-resolution image is generated from a low-resolution image, a trained annotator (Annot.) model 112 of the AI models 104 can annotate the high-resolution image, as also described herein.

In the example implementation of FIG. 1, the converted high-resolution image is maintained in a suitable data store 114, typically a PACS (picture archiving and communication system) data store. For example, an according to the DICOM (Digital Imaging and Communications in Medicine) standard (specifying a data interchange protocol, digital image format, and file structure) can be locally transcoded to JPEG format, and streamed to PACS 114, e.g., in an edge cloud storage location. The generated annotation data is maintained in an annotation data store 116, e.g., database with reference data associating the annotation to its counterpart high-resolution image, and storing the coordinates within the image to which the annotation is to be overlaid.

Once the data is maintained in the data stores 114 and 116, high-resolution image(s) can be pulled from the PACS data store 114 along with their corresponding annotation overlay(s). For example, a zero-footprint (ZFP) viewer 118 (which prevents hackers from accessing sensitive information and/or a data trail by removing or reducing the data footprint), can pull the data for rendering as annotation-overlaid image(s) on a suitable display device 120, such as incorporated into or couple to a radiologist's laptop computer. The radiologist can make a final determination after viewing the annotated high-resolution image(s). In general, annotation is not intended for final defect determination, but rather intended to be a tool to assist the radiologist if the radiologist decides to overlay the AI-generated annotation on the image.

With respect to security and privacy, consider that the MRI device 102 is coupled to an endpoint 122 (as indirectly depicted in FIG. 1) that acts as a transmission source for sending the low-resolution images to an edge cloud location 124, e.g., where model training and/or image conversion (low-resolution image-to-high-resolution image generation) occur. Because this data needs to be transmitted securely, even in an otherwise private (e.g., 5G) network, a reconfigurable intelligent surface 126 is inserted into the signal path to obtain the incoming data as incoming electromagnetic signals from the endpoint source 122, and hardware encrypt the electromagnetic signals prior to retransmission to the receiving entities. Only authorized receiving entities (e.g., user equipment that are aware of the hardware encryption) are able to understand (e.g., decrypt) the hardware-encrypted electromagnetic signals. Note that MRI image capture and storage is regulated, but annotation data is not regulated.

In general, a reconfigurable intelligent surface 126 (also referred to as a metasurface), is a manmade thin reflective or refractive surface whose electromagnetic response can be electronically controlled. Reconfigurable intelligent surfaces are characterized by their two-dimensional arrays of electronically controllable reflecting elements that can dynamically manipulate electromagnetic waves by altering attributes such as phase, amplitude, and direction of the incoming signal, as further described with reference to FIGS. 7-9.

Each metasurface typically is made up of (possibly up to) dozens, hundreds or thousands of unit-cells, and because the individual unit-cell can be controlled, reconfigurable intelligent surfaces can provide programmable and smart wireless environments. For example, one scenario is to use such a metasurface to intelligently reconfigure wireless communications, including for secure communications as described herein. For example, a controller (e.g., in the edgecloud 124/location) can change the characteristics of incoming signals from the endpoint 122 before retransmitting them, so that any unauthorized receiver attempting to redirect/tap into the retransmitted signals that does not know about the change in the signal characteristics is unable to interpret the received, retransmitted signals in a meaningful way. Note that unexpected redirection and/or tapping into the retransmitted signal (the path integrity is compromised by an eavesdropper) also can be detected by expected versus actual angle-of-arrival data/time-of-flight data, and/or by expected versus actual signal strength.

With respect to training, e.g., at the edge 124, training is based on data obtained from the MRI device 102, e.g., as maintained in the data stores 114 and 116. Training is further based on federated learning data obtained from the public cloud 128, including data that can be used for model initialization, aggregation (with other models) and model updating.

Figure 2:
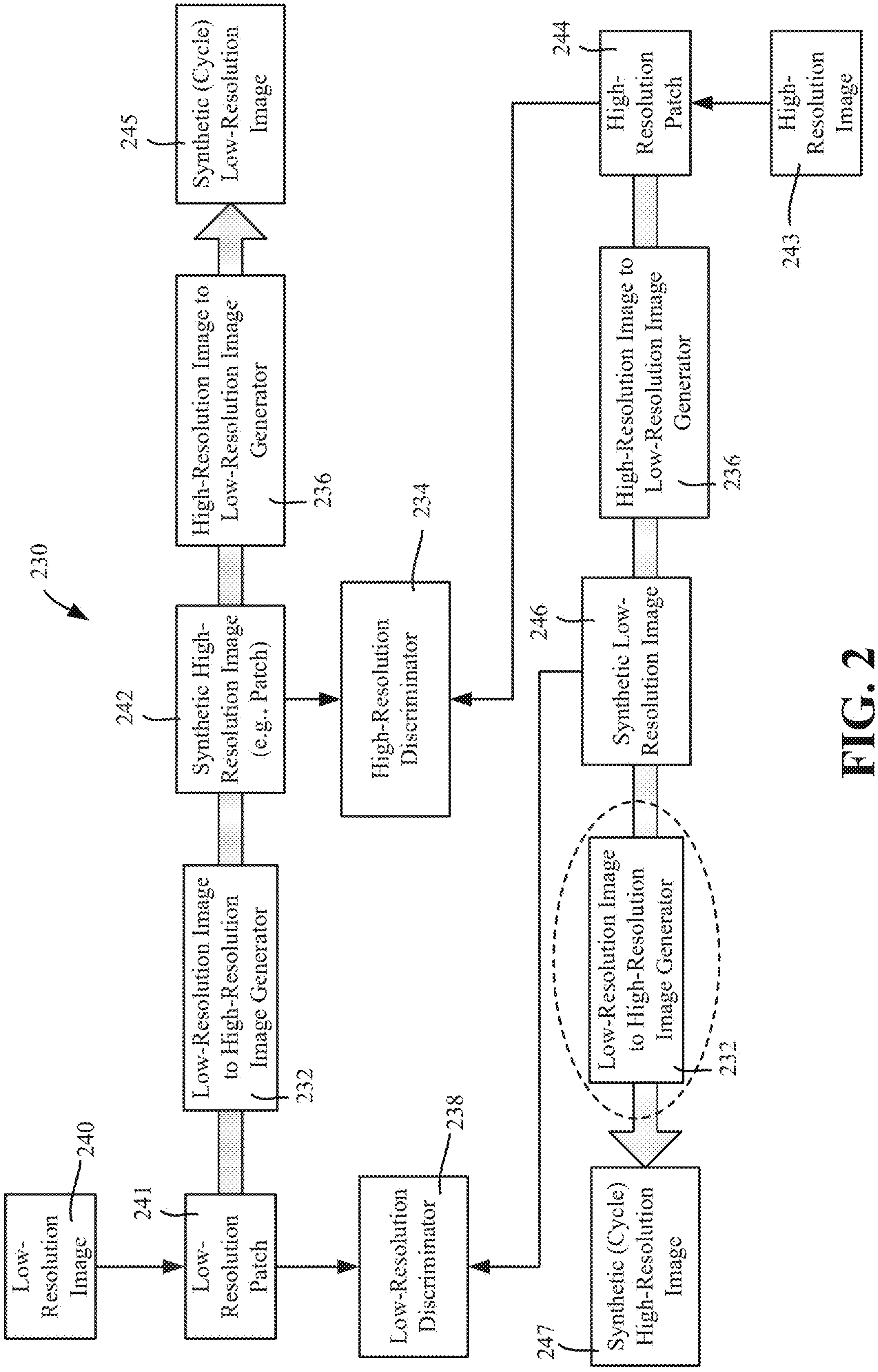
FIG. 2 is an example block diagram representation of training a low-resolution-to-high-resolution image generator model using a cycle generative adversarial network that includes the generator model, in accordance with various example embodiments and implementations of the subject disclosure.
Figure 3:
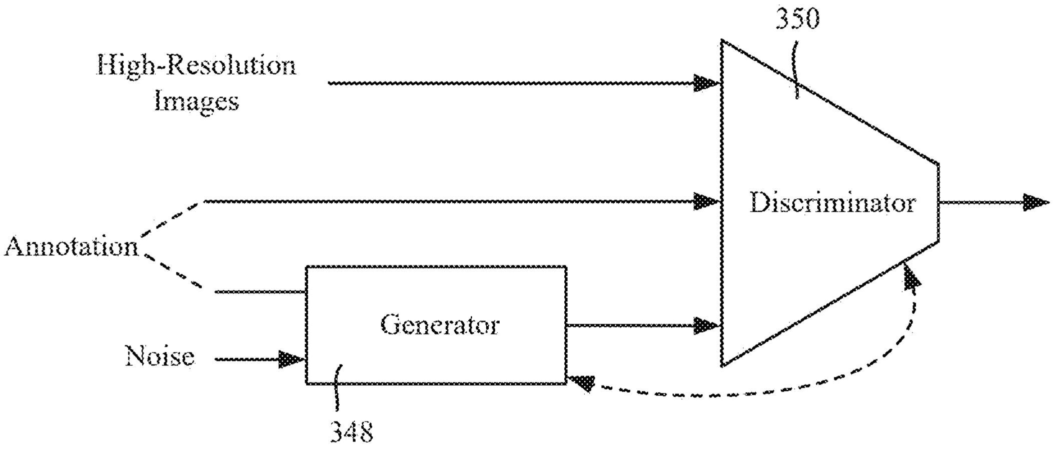
FIG. 3 is an example block diagram representation of training an annotator model for annotating high-resolution images based on a conditional generative adversarial network, in accordance with various example embodiments and implementations of the subject disclosure.
Figure 4:
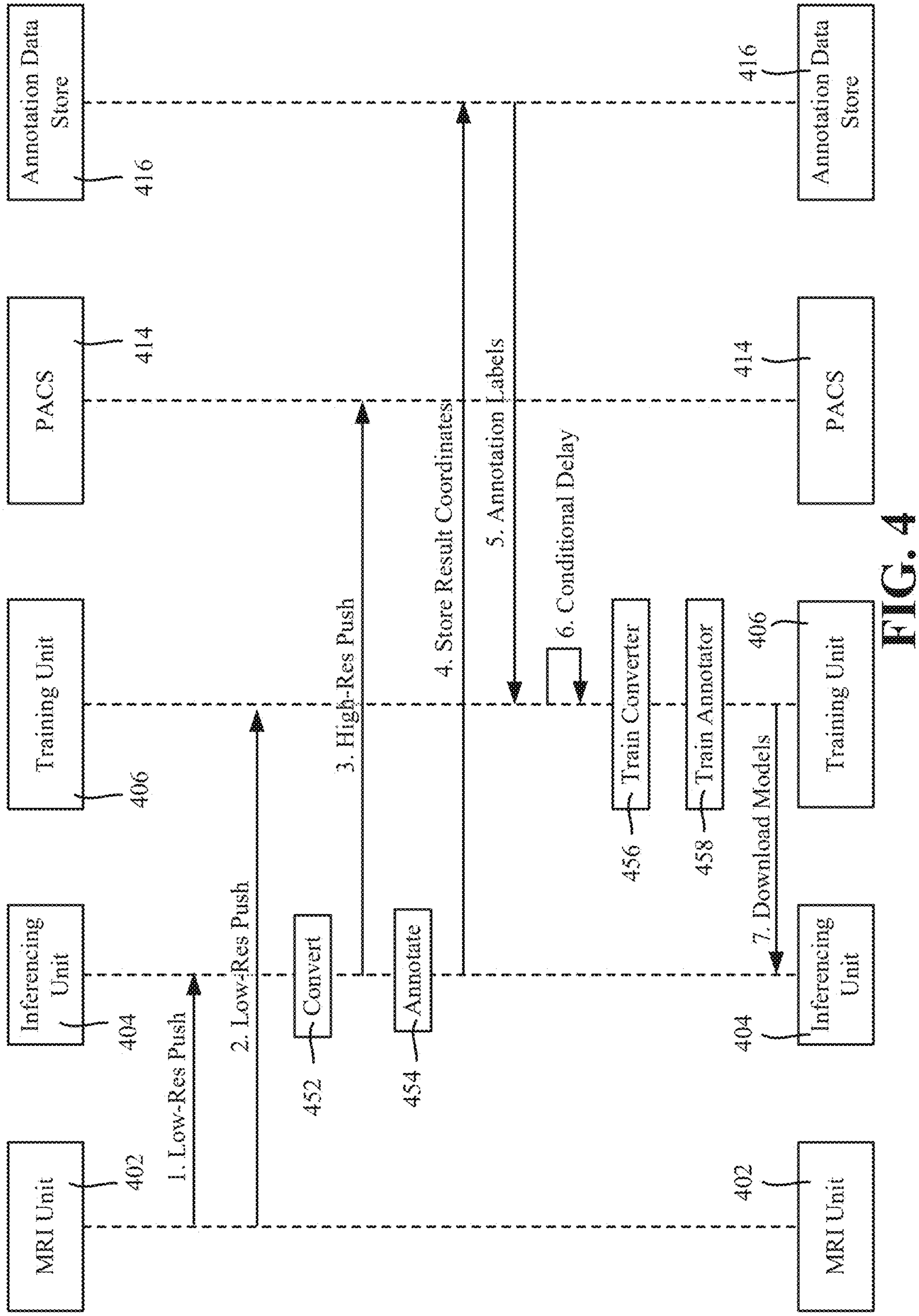
FIG. 4 is an example dataflow/sequence diagram edge of edge flow training of a low-resolution-to-high-resolution image generator and training of an annotator model, in accordance with various example embodiments and implementations of the subject disclosure.

FIGS. 2-4 provide additional details related to model training. More particularly, FIG. 2 is a block diagram representation of a cycle generative adversarial network (CycleGAN) 230 for training the low-resolution-to-high-resolution image generator model. A CycleGAN does not need labeled training samples, although for efficiency the training samples can be narrowed to a specific medical procedure (e.g., a knee MRI scan, an MRI scan related to an infant, and so on), with a model trained for that specific procedure.

In general, the CycleGAN 230 includes a low-resolution-to-high-resolution image generator model 232, a high-resolution image discriminator model 234, a high-resolution-to-low-resolution image generator model 236, and a low-resolution image discriminator model 238. A low-resolution image 240 (e.g., a low-resolution patch 241 therein) is input to the low-resolution-to-high-resolution image generator model 232, resulting in a synthetic high-resolution image 242, which is one input to the high-resolution discriminator 234. The other input to the high-resolution discriminator 234 is from a high-resolution image 243 (e.g., input as a counterpart high-resolution patch 244). The synthetic high-resolution image 242 is also downscaled by the high-resolution-to-low-resolution image generator model 236, which thereby produces a different synthetic low-resolution image 246.

The high-resolution discriminator 234 compares the synthetic high-resolution image (patch) 242 with an actual high-resolution image (of the same patch) 244, and provides results of a loss calculation based on differences between the input images 242 and 244. Over many training epochs with different data samples, learning based on this loss calculation results in less and less differences/losses as the high-resolution-to-low-resolution image generator model 236 learns to generate synthetic images that get closer and closer to the actual original images.

In the inverse, the actual high-resolution image patch 244 is input to the high-resolution-to-low-resolution image generator model 236, which produces a synthetic low-resolution image 245, which is one input to the low-resolution discriminator 238. The other input to the low-resolution discriminator 234 is the actual low-resolution image patch 241. The synthetic low-resolution image 246 is also upscaled by the low-resolution-to-high-resolution image generator model 232 which produces a different synthetic high-resolution image 246.

The low-resolution discriminator 238 compares the synthetic low-resolution image (patch) 246 with the actual low-resolution image (of the same patch) 241, and provides results of its own loss calculation based on differences between the input images 241 and 246. As in the other direction, over many training epochs with different data samples, learning based on this other loss calculation results in less and less differences/losses as the high-resolution-to-low-resolution image generator model 236 learns to generate low-resolution synthetic images that get closer and closer to the actual original low-resolution images.

Thus, initially the generators 232 and 236 are not particularly good, such that it is easy for the discriminators 234 and 238, respectively, to differentiate the actual images from the synthesized images. However, over multiple training epochs of many images/patches of images, the generators 232 and 236 get better and better until each generator reaches a point in which their respective generator cannot significantly distinguish between the synthesized images and the actual images. More particularly, a loss threshold in each generator is satisfied, that is, each calculated loss drops to below a loss threshold, whereby the generators 232 and 236 have reached a stability point. At this point, the low-resolution image to high-resolution image generator 232 (inside the dashed elliptical shape) is sufficiently trained for use in generating highly-accurate high-resolution images suitable for medical expert analysis, (assuming that a sufficient number of good training samples in terms of size and variety were available).

FIG. 3 shows training of the annotator model 110, in which a generator 348 generates annotations for a discriminator 350 in a conditional generative adversarial network. The generator 348 selectively adds noise to annotation data to try and deceive the discriminator 350, which inputs actual annotation data and high-resolution images to be annotated for comparison with the generator-produced annotation data. Over multiple training samples, the discriminator 350 improves in its ability to differentiate actual from generated annotations, while at the same time the generator 348 learns from the discriminator comparison results to generate better and better annotations that are more difficult to differentiate. Eventually, the generator 348 is fully trained to where its generated annotation data satisfies a loss threshold when compared to actual annotation data, and is thus ready for inferencing upon deployment.

It should be noted that the annotator model training is specific to a medical procedure as described above, that is, the training high-resolution images and annotation data input are narrowed to a specific scanning purpose. Further note that the overlaid annotation can be any visible representation that is suitable to point out/highlight to the medical expert a particular location in the image that is indicative of a likely defect (if any), e.g., a red dot, semi-transparent highlighted area, a line, circled area or other color/shape, a colored arrow, text, and so forth.

FIG. 4 is an example dataflow/sequence diagram generally directed to edge training (updating) of the low-resolution-to-high-resolution image generator, and training of the annotator model. Arrows one (1) and (2) represent an MRI unit 402 pushing the low-resolution image to an inferencing unit 404 and a training unit 406, respectively.

Block 452 represents the AI inferencing unit 404 upscaling the low-resolution image to the high-resolution image, which is sent to the PACS datastore 414 (arrow three (3)). Block 452 represents the AI inferencing unit 404 annotating the high-resolution image, with annotation data (result coordinates) stored in the annotation data store 416 (arrow four (4)).

For training to update the inferencing unit 404, in addition to the low-resolution image obtained by the training unit 406 via arrow two (2), annotation labels are obtained by the training unit 406 as represented by arrow five (5). Note that one implementation of the trained annotator is trained via a conditional GAN, whereby arrow six (6) shows conditional delay.

Blocks 456 and 458 respectively represent training the image converter model (low-resolution image-to-high-resolution image generator) and the annotator model, as described with reference to FIGS. 2 and 3, respectively. Once trained, (e.g., updated), the models are downloaded to the inferencing unit 404 as represented by arrow seven (7) for use in subsequent image generation and annotation.

Figure 5:
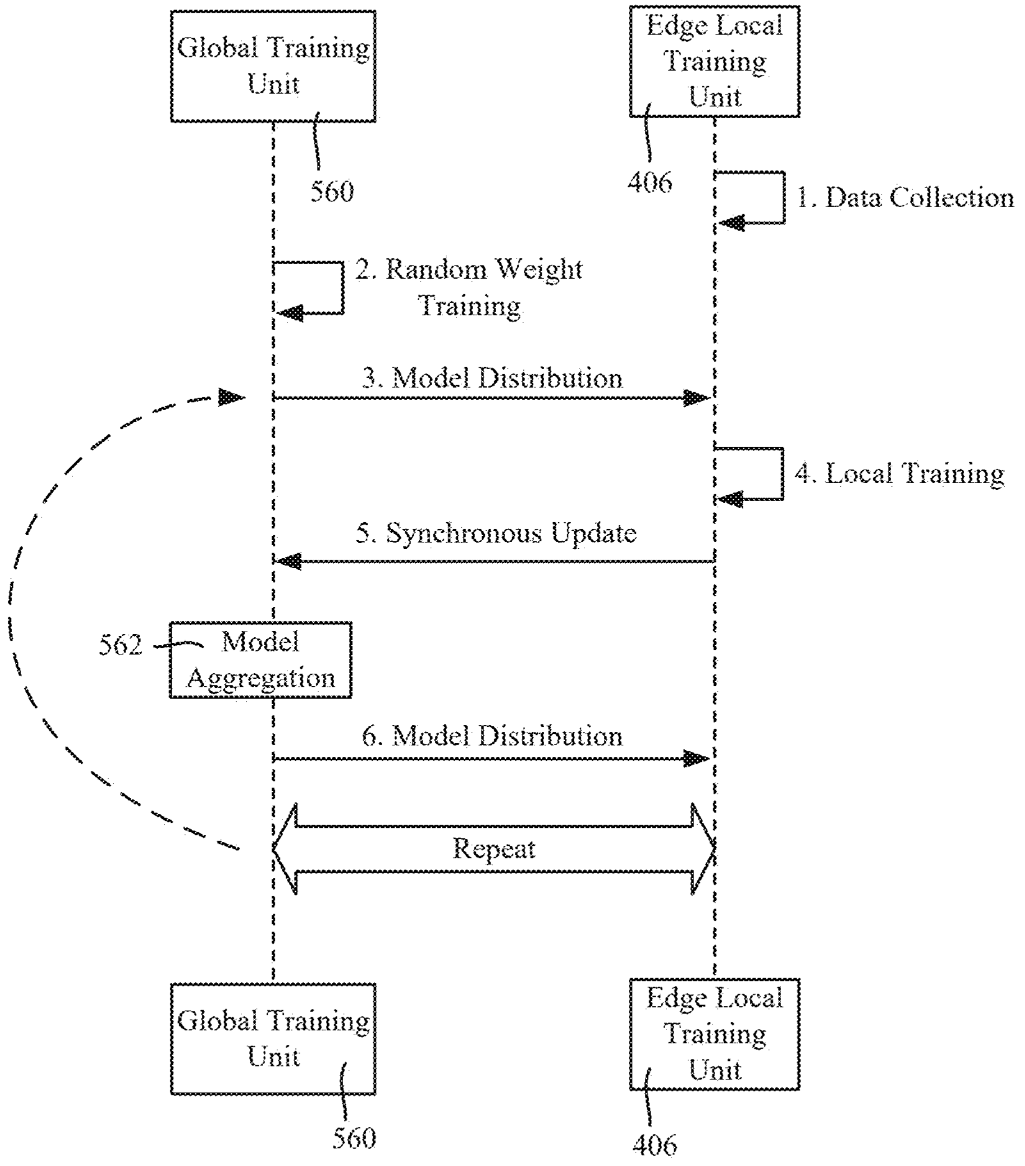
FIG. 5 is a representation of a dataflow/sequence diagram related to federated learning (involving a public cloud) for assisting in edge local model training, in accordance with various example embodiments and implementations of the subject disclosure.

FIG. 5 shows edge local training based on federated learning with respect to global data from a global training unit 560, e.g., in the public cloud 128 (FIG. 1). Data collection is performed by the edge local training unit 406 at arrow one (1). Random weight training is performed by the global training unit 560 at arrow two (2), which results in model(s) distributed to the edge local training unit 406 (and other edge training unit instances) at arrow three (3).

Arrow four (4) represents the edge local training unit 406 performing training as generally described herein, with the benefit of the global data obtained from the global training unit 560. Once trained, the edge local training unit 406 participates in federated learning by providing a synchronous update (arrow five (5)) of its model data to the global training unit 560. With this model update data, the global training unit 560 performs model aggregation (block 562) with other models' data to obtain updated and aggregated model data, which is distributed back to the edge local training unit 406 (and other edge training unit instances) at arrow six (6). The process repeats on demand as needed, e.g., periodic drift detection can trigger a retraining.

Figure 6:
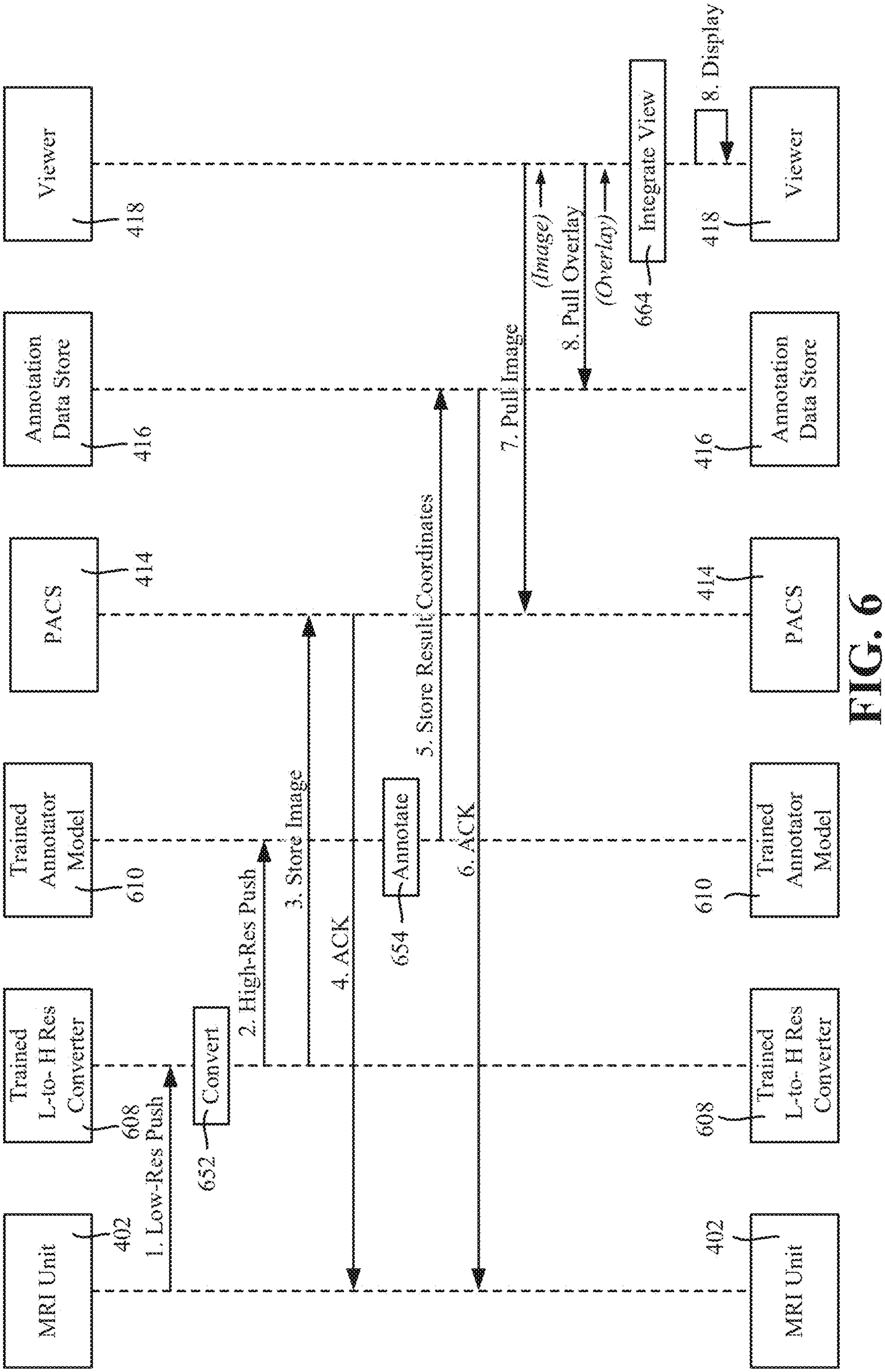
FIG. 6 is an example dataflow/sequence diagram of edge-based inferencing to convert a low-resolution image to a high-resolution image and annotate the high-resolution image, in accordance with various example embodiments and implementations of the subject disclosure.

FIG. 6 is an example dataflow/sequence diagram of edge flow inferencing by the trained models that converts (block 652) a low-resolution image to a high-resolution image and annotates (block 654) the high-resolution image. Arrow one (1) represents the MRI unit 402 pushing the low-resolution image to the trained low-resolution-to-high-resolution converter model 608, (e.g., the low-resolution-to-high-resolution generator resulting from FIG. 2's CycleGAN training), for converting at block 652. This synthetic (but highly-accurate) high-resolution image is pushed to the trained annotator model 610 (arrow two (2)), and stored in the PACS storage 414 (arrow three (3)), which returns an ACK (acknowledge) message to the MRI unit 402 (arrow four (4)).

Block 654 represents the trained annotator model 610 annotating the generated high-resolution image, which results in coordinates stored in the annotation data store 416 in association with a reference identifier or the like to the matching image. The annotation data store 416 returns an ACK (acknowledge) message (arrow six (6)) in response to storing the annotation data.

Arrows seven (7) and eight (8) represent a viewer device/program, at any given time, pulling (requesting and receiving) an image from the PACS 414 and its related overlay from the annotation data store 416. Block 418 represents the overlaid image being displayed by the viewer 418 on a display device coupled thereto.

Figure 7:
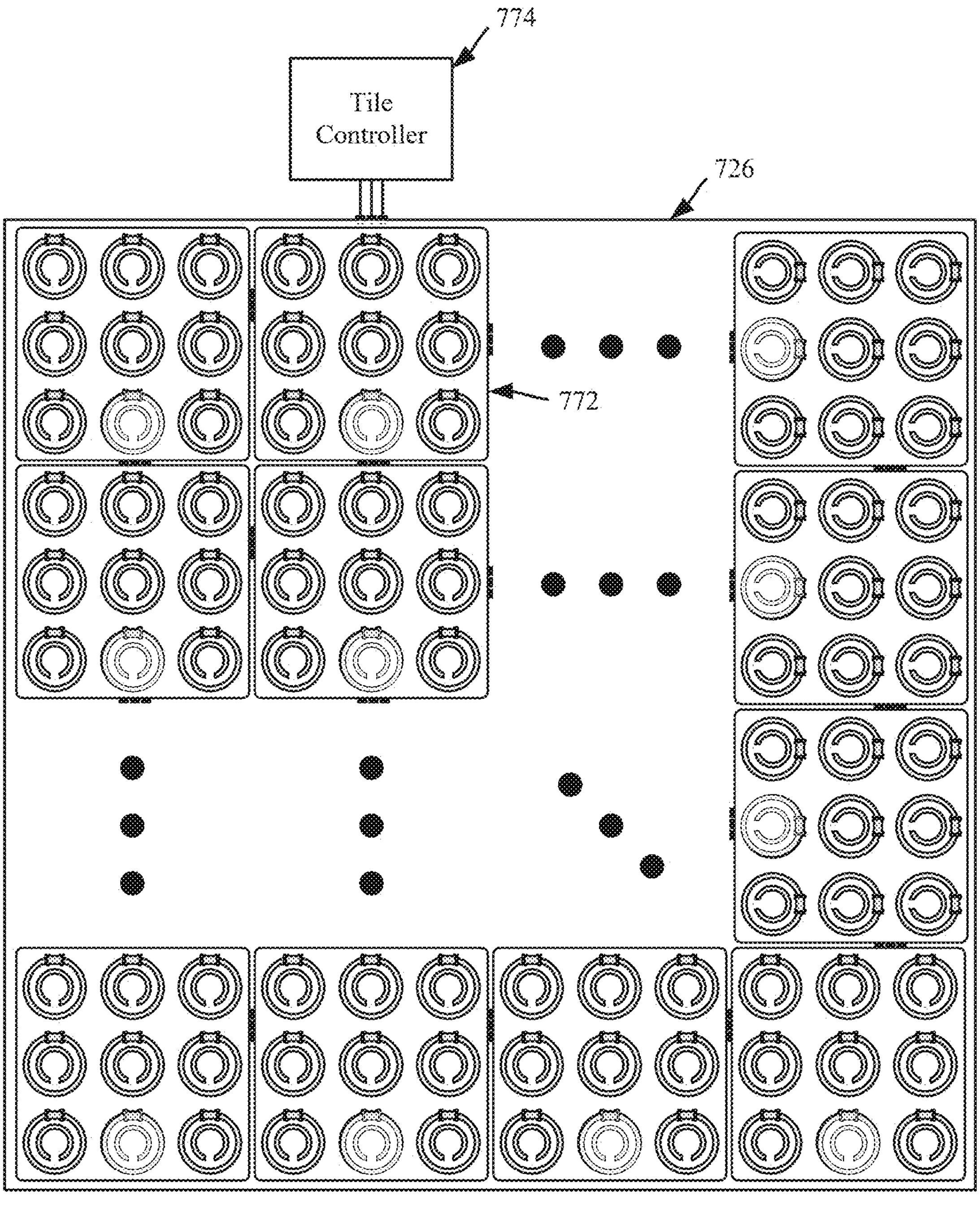
FIG. 7 is a representation of example subarrays that can be connected together to form a higher order m×n reconfigurable intelligent surface array, in accordance with various embodiments and implementations of the subject disclosure.

FIG. 7 is a representation of an example reconfigurable intelligent surface 726 assembled from modules of subarrays (e.g., of 3×3 unit cells). One subarray 772 of the subarray modules is labeled; the other subarray modules are not labeled for purposes of clarity. Note that having subarrays that are modular is not a requirement, nor is having subarrays of the same size or the same number of unit cells in each dimension, however modular subarrays provide benefits in manufacturing, and symmetrical, same-sized subarrays simplify reflection pattern (e.g., closed-form equations) design and reflected signal strength design.

In FIG. 7, multiple modules of j×k (3×3 in this example) unit cells are connected together to form a higher order m×n reconfigurable intelligent surface array. Significantly, multiple of these modules can be coupled together to form a higher order array using coupling terminals so that any vertically or horizontally adjacent module can be coupled thereto, as well as a tile controller 774 (or other controller) that controls the hardware encryption. For example, the controller 774 can change characteristics of incoming signals (e.g., by adding variable delay times) before retransmitting them, so that any receiver that does not know the variable delay time pattern is unable to redirect/tap into the signals in a meaningful way.

A significant benefit of using a modular approach is scalability; larger reconfigurable intelligent surfaces with larger numbers of elements offer a higher gain to the reflected signal, and vice versa for less elements and lower gain. Hence, depending on the largest signal strength desired, the size of the reconfigurable intelligent surface can be scaled up or down based on the number of modules. For example, a small reconfigurable intelligent surface can be formed with a 2×2 array of modules or can be enlarged into an m×n array by adding modules. As little as a single module may be sufficient for some applications, e.g., if 25 unit cells are all that are needed for a low-signal strength application, a single 5×5 array of unit cells can be built into a module; (a "module" may not be needed; however an advantage of using a module as described herein allows for future expansion).

Figure 8A:
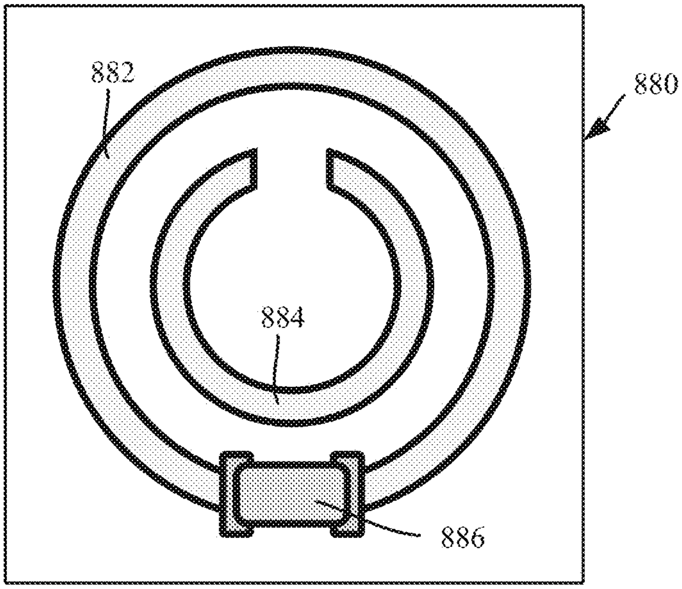
FIGS. 8A and 8B are example top view (FIG. 8A) and three-dimensional perspective view (FIG. 8B) representations of an example unit cell useable with a reconfigurable intelligent surface, in accordance with various embodiments and implementations of the subject disclosure.
Figure 8B:
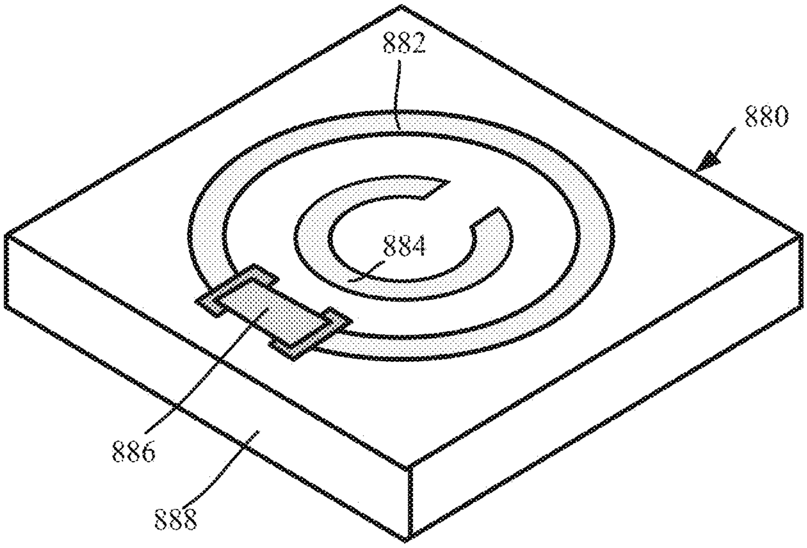

FIG. 8A shows an example design of a unit cell (or element) 880 that can be part of a reconfigurable intelligent surface/a module, in which a unit cell is a basic building block of the reconfigurable intelligent surface. By understanding and performing controlled adjustment of each unit cell's properties, the system can predict and manage the overall behavior of the reconfigurable intelligent surface.

In the example nonlimiting implementation shown in FIGS. 8A (top view) and 8B (three-dimensional perspective view), one design of the unit cell 880 comprises two circular split rings 882 and 884. The outer ring 882 has a tunable device 886, e.g., an integrated varactor that offers a tunable capacitance with voltage. The dimensions of these rings 882 and 884 can be tailored to specific operational frequency ranges for which the unit cell is designed. As is understood, shapes other than circular split rings (e.g., square, rectangular and so on) and other configurations can be used in the construction of a unit cell. These elements can be designed on a metallization layer on a (e.g., low-cost) substrate 888 (FIG. 2B).

Figure 9:
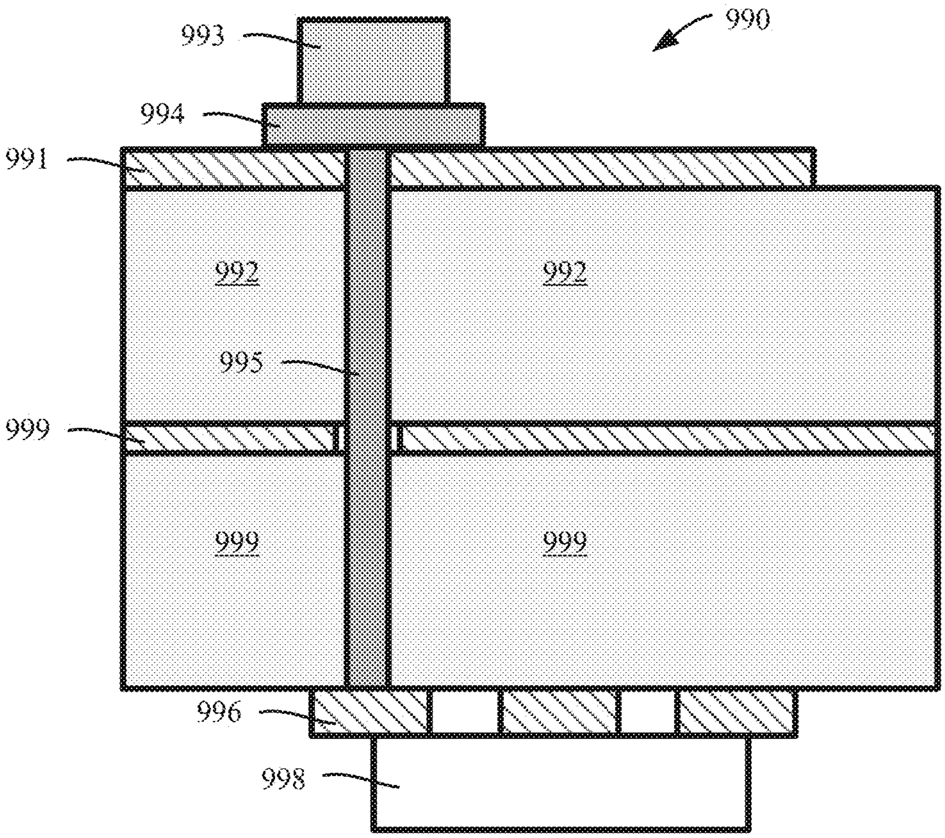
FIG. 9 is a cross-sectional view of an example unit cell usable with a reconfigurable intelligent surface, showing a stack and arrangement of fabricated layers, in accordance with various embodiments and implementations of the subject disclosure.
Figure 10A:
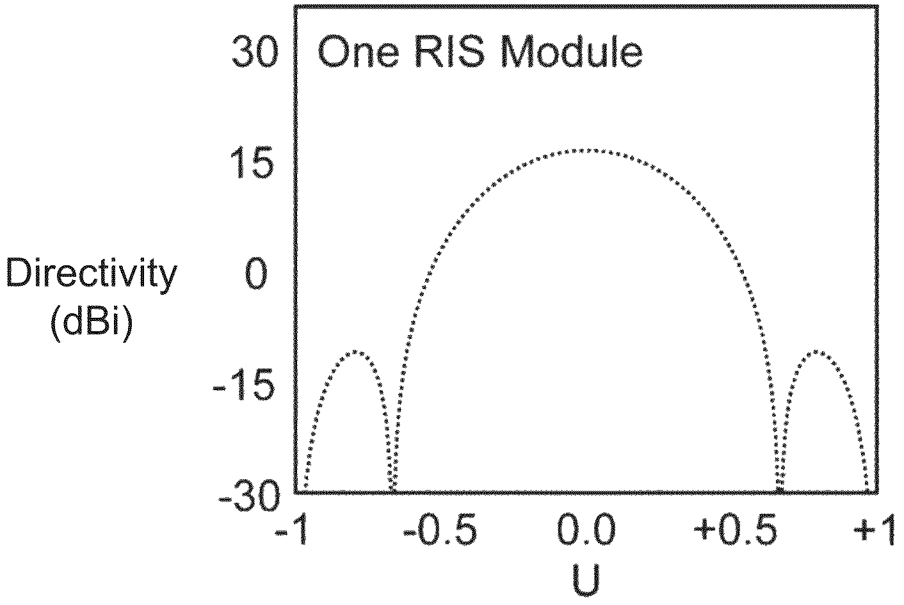
FIG. 10A is an example directivity diagram showing the signal gain and main lobe corresponding to one reconfigurable intelligent surface module (a 3×3 array of unit cells), in accordance with various embodiments and implementations of the subject disclosure.
Figure 10B:
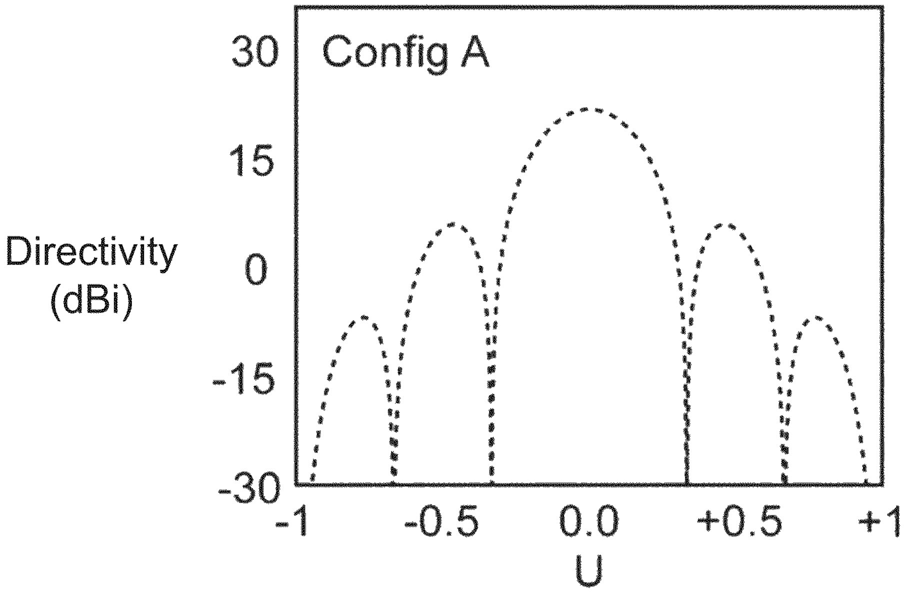
FIG. 10B is an example directivity diagram showing the signal gain and main lobe corresponding to one reconfigurable intelligent surface configuration (a 6×6 array), in accordance with various embodiments and implementations of the subject disclosure.

FIG. 9 shows a cross-sectional side view of a nonlimiting fabrication layer stack and arrangement of a unit cell 990. A top metallization layer 991 is patterned on a first substrate layer 992. The unit cells/elements are designed on each cell's metallization layer 991. The surface mounted device (SMD) tunable device (e.g., varactor) 993 can be soldered on top of SMD pads 994 atop the metallization layer 991, with a via 995 (e.g., for voltage control connections of the tunable device 993) to a bottom metallization layer 996 that couples to a microcontroller and power supply controller (PSU)/distribution module 998, as well as circuitry related to hardware encryption (although hardware encryption circuitry may be on a per-subarray basis, or for the entire reconfigurable surface).

The underside of the first substrate layer 992 is separated from a second substrate layer 999 by a metal plane 999 acting as RF ground. Below the underside of the second substrate layer 998 is the bottom metallization layer 996 which is patterned to form the DC biasing and control circuitry. The microcontroller and the PSU/power distribution module 998 are soldered on this bottom metallization layer 996. To ensure seamless interconnection across the multi-layered stack, the via 995 is strategically positioned. For instance, the tunable device 993 (e.g., varactor) is linked to two vias (only one via 995 is represented in the example of FIG. 9): one via connecting its negative terminal to the ground plane 999, while the other via links its positive terminal to the biasing on the bottom metal layer 996.

Figure 11A:
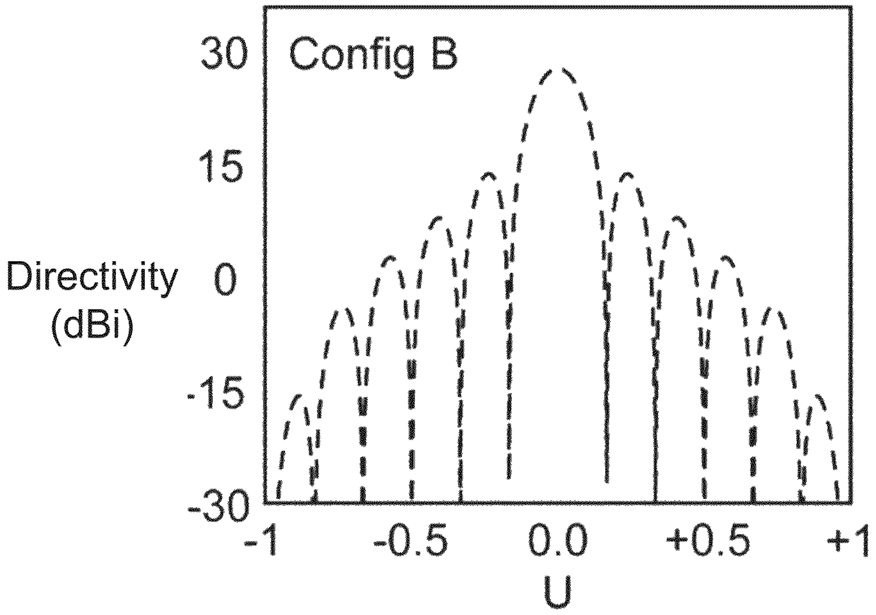
FIG. 11A is an example directivity diagram showing the signal gain and main lobe corresponding to another reconfigurable intelligent surface configuration (a 12×12 array), in accordance with various embodiments and implementations of the subject disclosure.
Figure 11B:
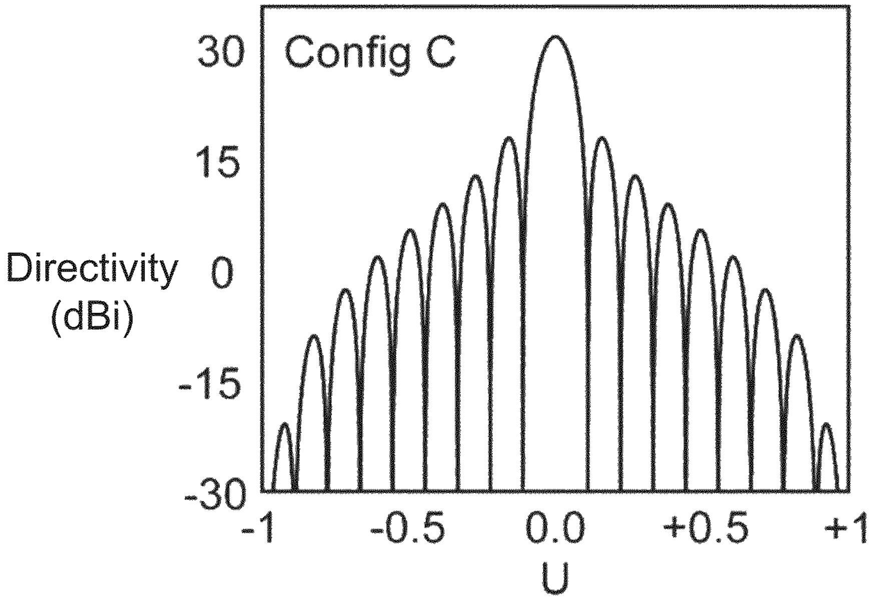
FIG. 11B is an example directivity diagram showing the signal gain and main lobe corresponding to yet another reconfigurable intelligent surface configuration (an 18×18 array), in accordance with various embodiments and implementations of the subject disclosure.

FIGS. 10A, 10B, 11A and 11B show the directivity diagrams of the reflected signal from the reconfigurable intelligent surface aperture in different configurations, namely with one reconfigurable intelligent surface module (3×3 array) (FIG. 10A), configuration "A" (6×6 array) (FIG. 10B), configuration "B" (12×12 array) (FIG. 11A), and configuration "C" (18×18 array) (FIG. 11B). As can be seen, as the number of elements is increased in the reconfigurable intelligent surface array, the signal gain consequently increases, while the main lobe of the reflected beam subsequently becomes narrower.

Figure 12:
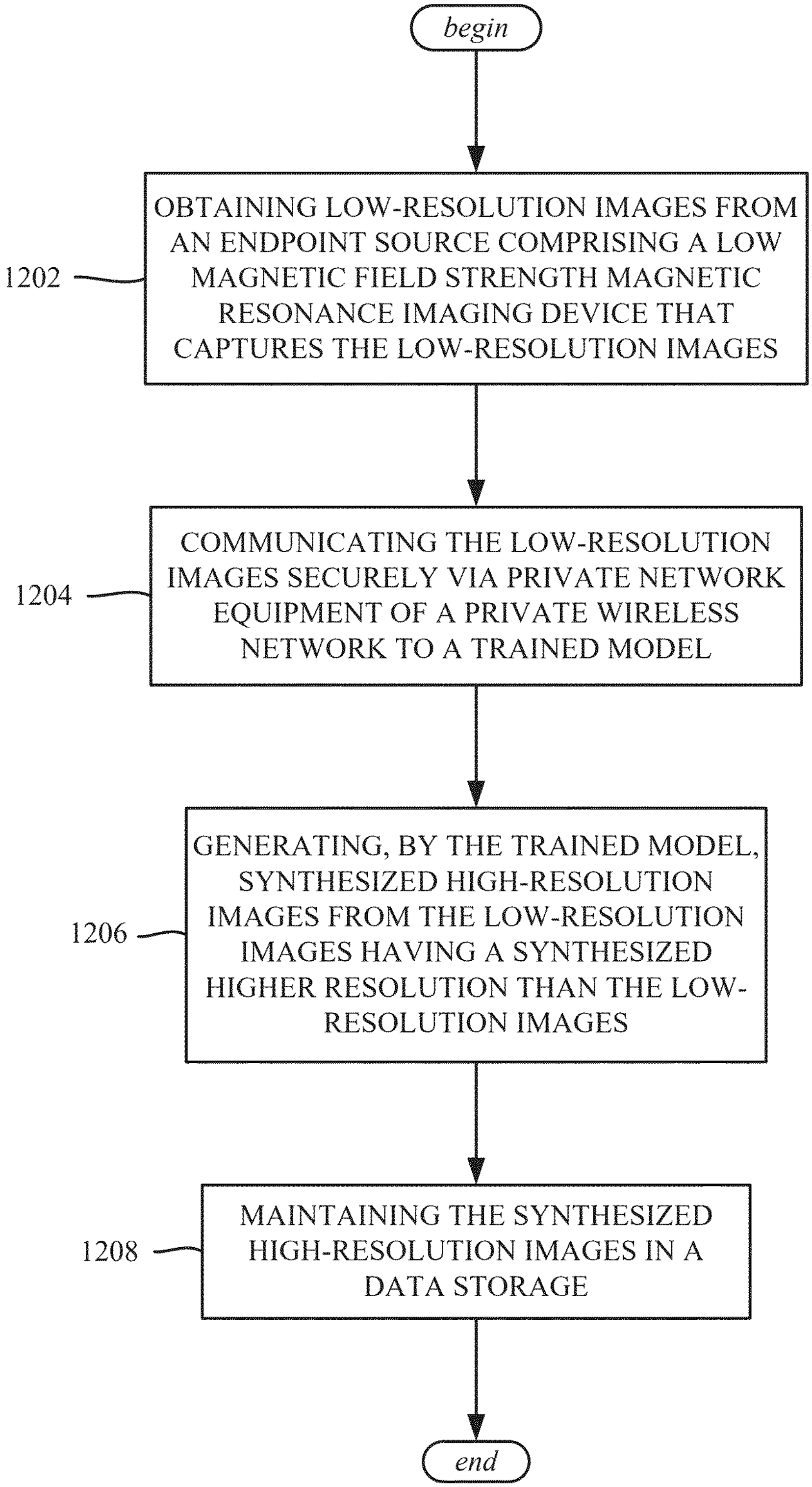
FIG. 12 is a flow diagram showing example operations related to generating synthesized high-resolution images from low-resolution images via a trained model, in accordance with various example embodiments and implementations of the subject disclosure.

One or more concepts described herein can be embodied in network equipment, such as represented in the example operations of FIG. 12, and for example can include at least one memory that stores computer executable components and/or operations, and at least one processor that executes computer executable components and/or operations stored in the memory. Example operations can include operation 1202, which represents obtaining low-resolution images from an endpoint source comprising a low magnetic field strength magnetic resonance imaging device that captures the low-resolution images. Example operation 1204 represents communicating the low-resolution images securely via private network equipment of a private wireless network to a trained model. Example operation 1208 represents generating, by the trained model, synthesized high-resolution images from the low-resolution images having a synthesized higher resolution than the low-resolution images. Example operation 1208 represents maintaining the synthesized high-resolution images in a data storage.

Communicating the low-resolution images securely via the private network equipment of the private wireless network to the trained model can include disaggregating the endpoint from the trained model via a reconfigurable intelligent surface in the wireless signal path between the endpoint source and the trained model.

The trained model can be a first trained model, and further operations can include inputting the synthesized high-resolution images into a second trained model, generating, by the second trained model, respective annotation data corresponding to respective defects detected by the second trained model in respective synthesized high-resolution images of the synthesized high-resolution images, and maintaining the respective annotation data in association with respective location data of respective locations in the respective synthesized high-resolution images, for subsequent viewing of a representation of an annotation of the respective annotation data at a respective location of the respective locations in conjunction with subsequent viewing of a respective synthesized high-resolution image of the respective synthesized high-resolution images.

Further operations can include training the second trained model based on medical procedure-specific data representative of images of a specific medical procedure.

The low magnetic field strength magnetic resonance imaging device can output a magnetic field strength of less than one Tesla.

The low magnetic field strength magnetic resonance imaging device can output a magnetic field strength between about 0.4 Tesla and about 0.6 Tesla.

Further operations can include retraining the trained model into an updated trained model based on the low-resolution images securely communicated via the private network equipment of the private wireless network, and based on high-resolution images from the data storage, comprising at least some of the synthesized high high-resolution images.

Retraining the trained model can be further based on federated learning data obtained from public network equipment of a public cloud. The federated learning data can be first federated learning data, and further operations can include, communicating second federated learning data, based on the updated trained model, to the public cloud.

The trained model can include a low-resolution-to-high-resolution image generator model of a generative adversarial network.

The generative adversarial network can include a cycle generative adversarial network comprising the low-resolution-to-high-resolution image generator model, a high-resolution image discriminator model, a high-resolution-to-low-resolution image generator model, and a low-resolution image discriminator model.

Further operations can include training the low-resolution-to-high-resolution image generator model based on the low-resolution images securely communicated via the private network equipment of the private wireless network, and based on high-resolution images from the data storage, wherein the training of the low-resolution-to-high-resolution image generator model can include performing iterations over a number of respective epochs until a loss threshold stopping criterion is satisfied, the performing of the iterations can include inputting respective low-resolution patches from the low-resolution images into the low-resolution-to-high-resolution image generator model to obtain respective synthetic high-resolution patch images, inputting the respective synthetic high-resolution patch images and actual respective high-resolution patch images into the high-resolution image discriminator model, inputting respective high-resolution patches from high-resolution images into the high-resolution-to-low-resolution image generator model to obtain respective synthetic low-resolution patch images, and inputting the respective synthetic low-resolution patch images and actual respective low-resolution patch images into the low-resolution image discriminator model.

Figure 13:
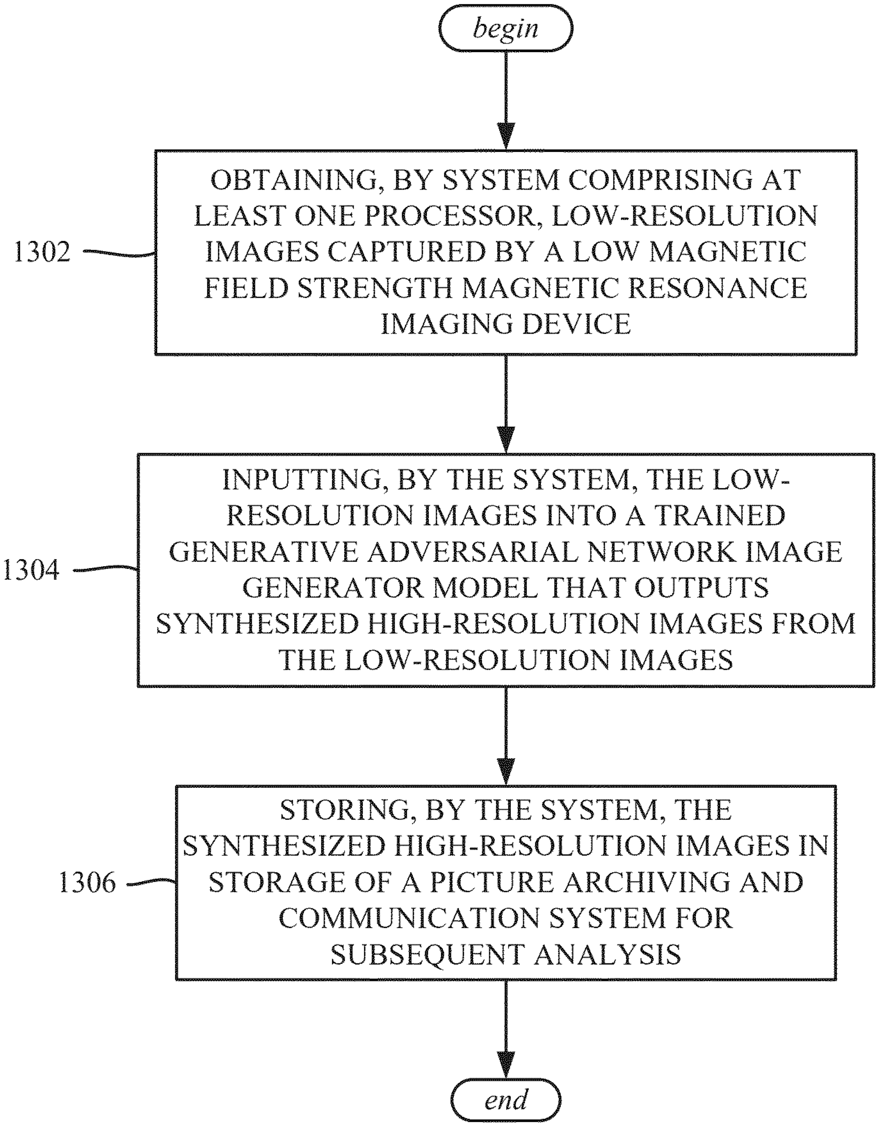
FIG. 13 is a flow diagram showing example operations related to inputting low-resolution images into a trained generative adversarial network image generator model that outputs synthesized high-resolution images from the low-resolution images, in accordance with various example embodiments and implementations of the subject disclosure.

One or more example implementations and embodiments, such as corresponding to example operations of a method, are represented in FIG. 13. Example operation 1302 represents obtaining, by system comprising at least one processor, low-resolution images captured by a low magnetic field strength magnetic resonance imaging device. Example operation 1304 represents inputting, by the system, the low-resolution images into a trained generative adversarial network image generator model that outputs synthesized high-resolution images from the low-resolution images. Example operation 1306 represents storing, by the system, the synthesized high-resolution images in storage of a picture archiving and communication system for subsequent analysis.

Obtaining the low-resolution images can include communicating with an endpoint source to receive the low-resolution images securely via a private wireless network.

The trained model can be a first trained model, and further operations can include inputting, by the system, a synthesized high-resolution image of the synthesized high-resolution images into a second trained model that outputs annotation data corresponding to a defect detected by the second trained model within the synthesized high-resolution image, and maintaining the annotation data in association with coordinates located in the synthesized high-resolution image, for overlaying the synthesized high-resolution image with the annotation data at a location based on the coordinates during subsequent viewing of the synthesized high-resolution image.

Further operations can include training, by the system, the trained generative adversarial network image generator model using a cycle generative adversarial network that can include the trained generative adversarial network image generator model.

Further operations can include obtaining, by the system, federated learning data corresponding to at least one other trained model, wherein the training of the trained generative adversarial network image generator model is further based on the federated learning data.

Figure 14:
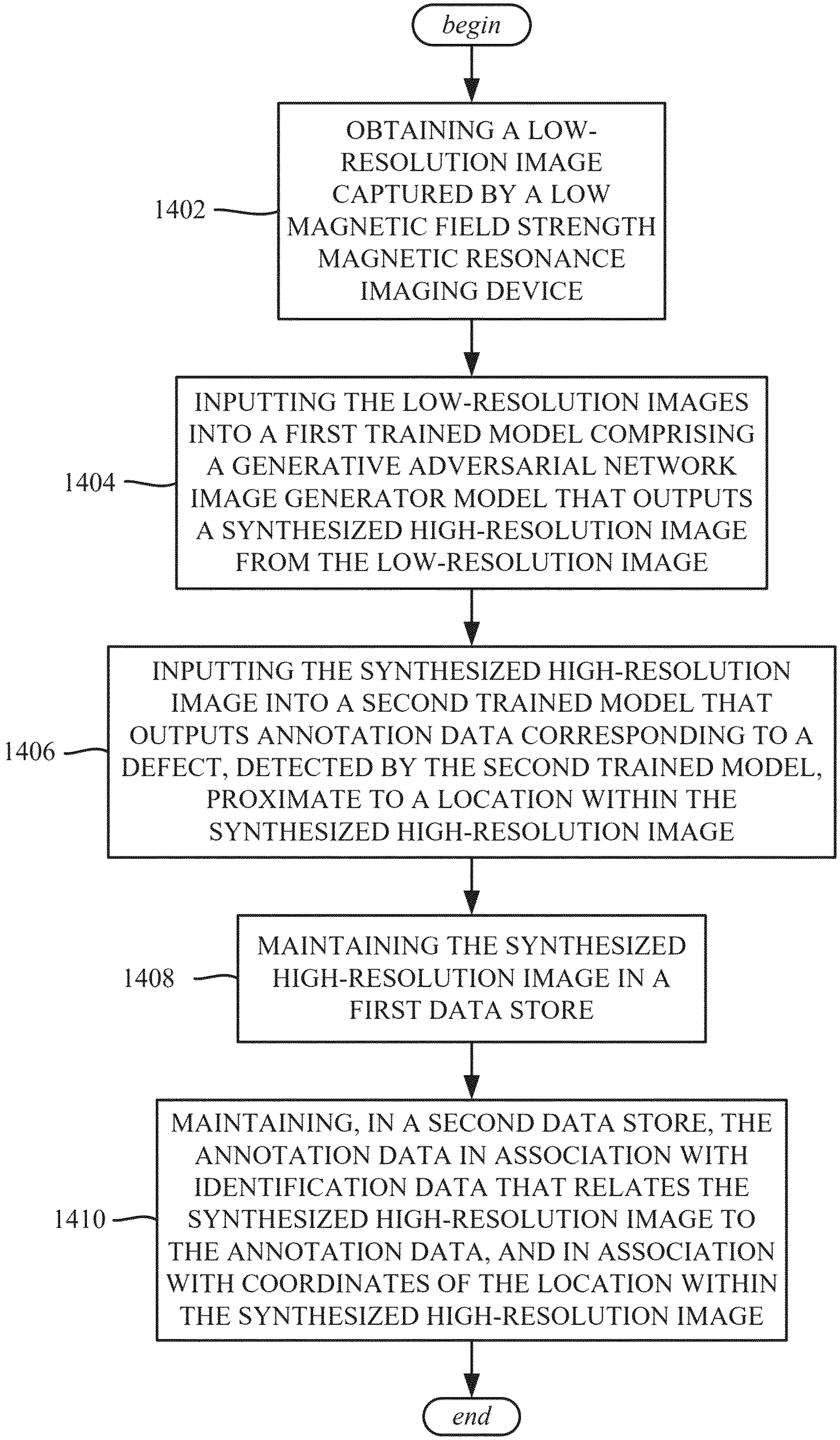
FIG. 14 is a flow diagram showing example operations related to using one models that outputs a high-resolution image from a low-resolution image, and another model that annotates the high-resolution image, in accordance with various example embodiments and implementations of the subject disclosure.

FIG. 14 summarizes various example operations, e.g., corresponding to a machine-readable medium, comprising executable instructions that, when executed by at least one processor of network equipment, facilitate performance of operations. Example operation 1402 represents obtaining a low-resolution image captured by a low magnetic field strength magnetic resonance imaging device. Example operation 1404 represents inputting the low-resolution images into a first trained model comprising a generative adversarial network image generator model that outputs a synthesized high-resolution image from the low-resolution image. Example operation 1406 represents inputting the synthesized high-resolution image into a second trained model that outputs annotation data corresponding to a defect, detected by the second trained model, proximate to a location within the synthesized high-resolution image. Example operation 1408 represents maintaining the synthesized high-resolution image in a first data store. Example operation 1410 represents maintaining, in a second data store, the annotation data in association with identification data that relates the synthesized high-resolution image to the annotation data, and in association with coordinates of the location within the synthesized high-resolution image.

Obtaining the low-resolution image can include communicating with an endpoint source to receive the low-resolution image securely over a private wireless network.

Further operations can include training the trained generative adversarial network image generator model using a cycle generative adversarial network that can include the trained generative adversarial network image generator model as a low-resolution-to-high-resolution image generator model, a high-resolution image discriminator model, a high-resolution-to-low-resolution image generator model, and a low-resolution image discriminator model.

As can be seen, the technology described herein is directed to upscaling low-resolution MRI images, which can have detected defects annotated for specific procedures, whereby lower-cost, lower-strength MRI devices can be highly useful in many medical scanning scenarios. Local training using a CycleGAN and based in part on federated learning provides a highly accurate low-resolution-to-high-resolution image generator model, while a conditional GAN provides a highly accurate annotator model. For security and privacy, a metasurface can be used for hardware signal encryption and/or signal path validation to mitigate potential unauthorized access or data interception.

The above description of illustrated embodiments of the subject disclosure, comprising what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As used in this application, the terms "component," "system," "platform," "layer," "selector," "interface," and the like are intended to refer to a computer-related resource or an entity related to an operational apparatus with one or more specific functionalities, wherein the entity can be either hardware, a combination of hardware and software, software, or software in execution. As an example, a component can be an apparatus with specific functionality provided by mechanical parts operated by electric or electronic circuitry. As yet another example, a component can be an apparatus that provides specific functionality through electronic components without mechanical parts, the electronic components can comprise a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

While the embodiments are susceptible to various modifications and alternative constructions, certain illustrated implementations thereof are shown in the drawings and have been described above in detail. It should be understood, however, that there is no intention to limit the various embodiments to the specific forms disclosed, but on the contrary, the intention is to cover all modifications, alternative constructions, and equivalents falling within the spirit and scope.

In addition to the various implementations described herein, it is to be understood that other similar implementations can be used or modifications and additions can be made to the described implementation(s) for performing the same or equivalent function of the corresponding implementation(s) without deviating therefrom. Still further, multiple processing chips or multiple devices can share the performance of one or more functions described herein, and similarly, storage can be effected across a plurality of devices. Accordingly, the various embodiments are not to be limited to any single implementation, but rather are to be construed in breadth, spirit and scope in accordance with the appended claims.

What is claimed is:

1. A system, comprising:

at least one processor; and at least one memory that stores executable instructions that, when executed by the at least one processor, facilitate performance of operations, the operations comprising:

obtaining low-resolution images from an endpoint source comprising a low magnetic field strength magnetic resonance imaging device that captures the low-resolution images;

communicating the low-resolution images securely via private network equipment of a private wireless network to a trained model;

generating, by the trained model, synthesized high-resolution images from the low-resolution images having a synthesized higher resolution than the low-resolution images; and maintaining the synthesized high-resolution images in a data storage, wherein the communicating of the low-resolution images securely via the private network equipment of the private wireless network to the trained model comprises disaggregating the endpoint source from the trained model via a reconfigurable intelligent surface in a wireless signal path between the endpoint source and the trained model.

2. The system of claim 1, wherein the trained model is a first trained model, and wherein the operations further comprise inputting the synthesized high-resolution images into a second trained model, generating, by the second trained model, respective annotation data corresponding to respective defects detected by the second trained model in respective synthesized high-resolution images of the synthesized high-resolution images, and maintaining the respective annotation data in association with respective location data of respective locations in the respective synthesized high-resolution images, for subsequent viewing of a representation of an annotation of the respective annotation data at a respective location of the respective locations in conjunction with subsequent viewing of a respective synthesized high-resolution image of the respective synthesized high-resolution images.

3. The system of claim 2, wherein the operations further comprise training the second trained model based on medical procedure-specific data representative of images of a specific medical procedure.

4. The system of claim 1, wherein the low magnetic field strength magnetic resonance imaging device outputs a magnetic field strength of less than one Tesla.

5. The system of claim 1, wherein the low magnetic field strength magnetic resonance imaging device outputs a magnetic field strength between 0.4 Tesla and 0.6 Tesla.

6. The system of claim 1, wherein the operations further comprise retraining the trained model into an updated trained model based on the low-resolution images securely communicated via the private network equipment of the private wireless network, and based on high-resolution images from the data storage, comprising at least some of the synthesized high-resolution images.

7. The system of claim 6, wherein the retraining of the trained model is further based on federated learning data obtained from public network equipment of a public cloud.

8. The system of claim 7, wherein the federated learning data is first federated learning data, and wherein the operations further comprise, communicating second federated learning data, based on the updated trained model, to the public cloud.

9. The system of claim 1, wherein the trained model comprises a low-resolution-to-high-resolution image generator model of a generative adversarial network.

10. The system of claim 9, wherein the generative adversarial network comprises a cycle generative adversarial network comprising the low-resolution-to-high-resolution image generator model, a high-resolution image discriminator model, a high-resolution-to-low-resolution image generator model, and a low-resolution image discriminator model.

11. The system of claim 10, wherein the operations further comprise training the low-resolution-to-high-resolution image generator model based on the low-resolution images securely communicated via the private network equipment of the private wireless network, and based on high-resolution images from the data storage, wherein the training of the low-resolution-to-high-resolution image generator model comprises performing iterations over a number of respective epochs until a loss threshold stopping criterion is satisfied, the performing of the iterations comprising:

inputting respective low-resolution patches from the low-resolution images into the low-resolution-to-high-resolution image generator model to obtain respective synthetic high-resolution patch images, inputting the respective synthetic high-resolution patch images and actual respective high-resolution patch images into the high-resolution image discriminator model, inputting respective high-resolution patches from high-resolution images into the high-resolution-to-low-resolution image generator model to obtain respective synthetic low-resolution patch images, and inputting the respective synthetic low-resolution patch images and actual respective low-resolution patch images into the low-resolution image discriminator model.

12. A method, comprising:

obtaining, by a system comprising at least one processor, low-resolution images captured by a low magnetic field strength magnetic resonance imaging device;

inputting, by the system, the low-resolution images into a trained generative adversarial network image generator model that outputs synthesized high-resolution images from the low-resolution images;

storing, by the system, the synthesized high-resolution images in storage of a picture archiving and communication system for subsequent analysis; and retraining the trained generative adversarial network image generator model into an updated trained generative adversarial network image generator model based on the low-resolution images securely communicated via private network equipment of a private wireless network, and based on high-resolution images, comprising at least some of the synthesized high-resolution images.

13. The method of claim 12, wherein the obtaining of the low-resolution images comprises communicating with an endpoint source to receive the low-resolution images securely via a private wireless network.

14. The method of claim 12, wherein the trained generative adversarial network image generator model is a first trained generative adversarial network image generator model, and further comprising inputting, by the system, one synthesized high-resolution image of the synthesized high-resolution images into a second trained generative adversarial network image generator model that outputs annotation data corresponding to a defect detected by the second trained generative adversarial network image generator model within the one synthesized high-resolution image, and maintaining the annotation data in association with coordinates located in the one synthesized high-resolution image, for overlaying the one synthesized high-resolution image with the annotation data at a location based on the coordinates during subsequent viewing of the one synthesized high-resolution image.

15. The method of claim 12, further comprising, training, by the system, the trained generative adversarial network image generator model using a cycle generative adversarial network that comprises the trained generative adversarial network image generator model.

16. The method of claim 15, further comprising obtaining, by the system, federated learning data corresponding to at least one other trained model, wherein the training of the trained generative adversarial network image generator model is further based on the federated learning data.

17. The method of claim 12, wherein the inputting of the low-resolution images to the trained generative adversarial network image generator model comprises disaggregating an endpoint source from the trained generative adversarial network image generator model via a reconfigurable intelligent surface in a wireless signal path between the endpoint source and the trained generative adversarial network image generator model.

18. A non-transitory machine-readable medium, comprising executable instructions that, when executed by at least one processor, facilitate performance of operations, the operations comprising:

obtaining a low-resolution image captured by a low magnetic field strength magnetic resonance imaging device;

inputting the low-resolution images into a first trained model comprising a generative adversarial network image generator model that outputs a synthesized high-resolution image from the low-resolution image;

inputting the synthesized high-resolution image into a second trained model that outputs annotation data corresponding to a defect, detected by the second trained model, proximate to a location within the synthesized high-resolution image;

maintaining the synthesized high-resolution image in a first data store; and maintaining, in a second data store, the annotation data in association with identification data that relates the synthesized high-resolution image to the annotation data, and in association with coordinates of the location within the synthesized high-resolution image, wherein the inputting of the low-resolution images to the first trained model comprises disaggregating an endpoint source from the first trained model via a reconfigurable intelligent surface in a wireless signal path between the endpoint source and the first trained model.

19. The non-transitory machine-readable medium of claim 18, wherein the obtaining of the low-resolution image comprises communicating with an endpoint source to receive the low-resolution image securely over a private wireless network.

20. The non-transitory machine-readable medium of claim 18, wherein the operations further comprise training the generative adversarial network image generator model using a cycle generative adversarial network that comprises the generative adversarial network image generator model as a low-resolution-to-high-resolution image generator model, a high-resolution image discriminator model, a high-resolution-to-low-resolution image generator model, and a low-resolution image discriminator model.

* * * * *